(12) United States Patent
Song et al.

(10) Patent No.: US 7,579,394 B2
(45) Date of Patent: Aug. 25, 2009

(54) ADHESION PROMOTER

(75) Inventors: Guiqin Song, Milton (CA); Nan-Xing Hu, Oakville (CA); T. Brian McAneney, Burlington (CA); Gordon Sisler, St. Catharines (CA)

(73) Assignee: Xerox Corporation, Norwalk, CT (US)

( * ) Notice: Subject to any disclaimer, the term of this patent is extended or adjusted under 35 U.S.C. 154(b) by 344 days.

(21) Appl. No.: 11/623,509

(22) Filed: Jan. 16, 2007

(65) Prior Publication Data

US 2008/0171826 A1    Jul. 17, 2008

(51) Int. Cl.
   *B60C 1/00*   (2006.01)
   *C08K 5/24*   (2006.01)
   *C08K 5/54*   (2006.01)

(52) U.S. Cl. .................. 524/261; 524/262; 524/263

(58) Field of Classification Search ............. 524/262, 524/261, 263; 526/935
   See application file for complete search history.

(56) References Cited

U.S. PATENT DOCUMENTS

| | | | |
|---|---|---|---|
| 4,029,827 A | 6/1977 | Imperial et al. | |
| 4,101,686 A | 7/1978 | Strella et al. | |
| 4,140,733 A | 2/1979 | Meyer, Jr. et al. | |
| 4,185,140 A | 1/1980 | Strella et al. | |
| 4,197,380 A | 4/1980 | Chao et al. | |
| 4,576,985 A | 3/1986 | Ono | |
| 4,618,640 A | 10/1986 | Tsuchida et al. | |
| 4,660,858 A | 4/1987 | Flanagan | |
| 4,712,808 A | 12/1987 | Beh-Forrest et al. | |
| 4,772,650 A | 9/1988 | Ou-Yang | |
| 4,942,195 A | 7/1990 | Flanagan et al. | |
| 5,021,499 A | 6/1991 | Tochinai et al. | |
| 5,037,874 A | 8/1991 | Nuttens et al. | |
| 5,057,561 A | 10/1991 | Manica et al. | |
| 5,063,271 A | 11/1991 | Jones | |
| 5,157,445 A | 10/1992 | Shoji et al. | |
| 5,401,791 A | 3/1995 | Milks | |
| 5,518,571 A | 5/1996 | Puerkner et al. | |
| 6,060,550 A | 5/2000 | Simon et al. | |
| 6,582,829 B1 | 6/2003 | Quinn et al. | |
| 6,794,443 B2 | 9/2004 | Chu et al. | |
| 6,797,774 B2 | 9/2004 | Kijima | |
| 6,800,680 B2 | 10/2004 | Stark et al. | |
| 6,833,404 B2 | 12/2004 | Quinn et al. | |
| 6,890,982 B2 | 5/2005 | Borsinger et al. | |
| 6,989,413 B2 | 1/2006 | Hazen et al. | |
| 2003/0108737 A1 | 6/2003 | Timmons et al. | |
| 2004/0102558 A1* | 5/2004 | Lin et al. | 524/417 |
| 2004/0185272 A1 | 9/2004 | Kaplan et al. | |
| 2005/0261416 A1* | 11/2005 | Morrison et al. | 524/487 |
| 2006/0008727 A1 | 1/2006 | Gervasi et al. | |
| 2007/0190345 A1* | 8/2007 | Sutter et al. | 428/448 |

OTHER PUBLICATIONS

U.S. Appl. No. 11/532,704, filed Sep. 18, 2006 in the name of Jyothsna Ram et al.

* cited by examiner

*Primary Examiner*—Mark Eashoo
*Assistant Examiner*—Angela C Scott
(74) *Attorney, Agent, or Firm*—Oliff & Berridge, PLC

(57) ABSTRACT

An adhesion promoter for a hot melt adhesive or a pressure sensitive adhesive prepared by admixing a hydrolytic silane compound with an aqueous buffer solution. The adhesive is able to bind at very low surface free energy substrates, such as Xerographic prints contaminated by silicone fuser oil. The hot melt adhesive maintains a substantially stable viscosity at temperature ranging from about 100° C. to about 200° C.

25 Claims, No Drawings

ADHESION PROMOTER

BACKGROUND

The present disclosure generally relates to adhesion promoters comprising a hydrolytic silane compound admixed with a aqueous buffer solution, and their use in methods for promoting adhesion of adhesives to a substrate. In embodiments, the adhesion promoter may be used in a hot melt adhesive or a pressure sensitive adhesive that is to be applied to a substrate.

The addition of the adhesion promoter to hot melt adhesives or pressure sensitive adhesives improves adhesion to very low surface free energy substrates. The admixed hydrolytic silane compound with aqueous buffer solution improves the thermal stability of the adhesive and the viscosity of the adhesive remains relatively constant at temperatures, for example, ranging from about 100° C. to about 200° C. The adhesive containing the admixed silane adhesion promoter is thus able to bind very low surface free energy substrates such as Xerographic prints contaminated with fuser oil, and maintains a substantially stable viscosity at adhesive application or operating temperatures from about 100° C. to 200° C.

REFERENCES

In a typical imaging device, a light image of an original to be copied is recorded in the form of a latent image upon a photosensitive member, and the latent image is subsequently rendered visible by the application of resin particles and pigment particles, or toner. The visible toner image is then in a loose powdered form and can be easily disturbed or destroyed. The toner image may be fixed or fused upon a support, which may be a support sheet such as plain paper, using a fuser roll.

To ensure and maintain good release properties of the fuser roll, it has become customary to apply release agents to the fuser roll during the fusing operation. Typically, these materials are applied as thin films of, for example, nonfunctional silicone oils or mercapto- or amino-functional silicone oils, to prevent toner offset.

U.S. Pat. No. 4,029,827 discloses the use of polyorganosiloxanes having mercapto functionality as release agents.

U.S. Pat. No. 4,101,686 and U.S. Pat. No. 4,185,140 disclose polymeric release agents having functional groups such as carboxy, hydroxy, epoxy, amino, isocyanate, thioether, or mercapto groups.

U.S. Pat. No. 5,157,445 discloses toner release oil having a functional organopolysiloxane.

Fuser oil unavoidably contaminates the surface of prints during Xerographic printing process. Because the fuser oil is chemically bound on the paper surface during the hot fusing process, especially for example with mercapto or amino functionalized fuser oil, it may be difficult to wipe off the fuser oil, and the surface free energy of the Xerographic prints is significantly lowered because of the oil contamination and thus causes poor binding between the adhesive and prints.

The adhesion may be improved by adding amino or mercapto functional hydrolytic silane compound or oligosiloxane silane to adhesives as adhesion promoters, but at the same time the silane may decrease the pot life of the adhesive. The viscosity may continuously increase during the application process at the application temperature such as from 100° C. to 200° C. The viscosity continuously increases and may cause operating problems.

In some extreme cases, such as Xerographic prints printed on the offset preprint forms, there is no commercial available adhesive that can be used to bind these kind of prints.

U.S. patent application Ser. No. 11/532,704, incorporated herein by reference in its entirety, describes an adhesion promoter comprising a silane compound and a release agent and/or adhesive.

While hot melt adhesives are known in the prior art, for example, U.S. Pat. No. 5,401,791 discloses bookbinding adhesives, U.S. Pat. No. 4,772,650 discloses bookbinding adhesive composition for book casemaking, U.S. Pat. No. 4,712,808 discloses bookbinding adhesive composition for hinge joint. U.S. Pat. No. 4,660,858 discloses bookbinding adhesive composition for book lining, U.S. Pat. No. 4,140,733 discloses polyethylene based bookbinding hot melt adhesives, they are all unsatisfactory in adhesive strength for perfect book binding applications when they are used for binding xerographic prints/paper substrates contaminated by fuser oils.

U.S. Pat. No. 6,800,680, U.S. Pat. No. 6,797,774, U.S. Pat. No. 6,794,443, U.S. Pat. No. 6,582,829, U.S. Pat. No. 5,518,571, U.S. Pat. No. 5,057,561 and U.S. Pat. No. 4,942,195, disclose varies kinds of polymers for hot melt adhesive application.

U.S. Pat. No. 6,989,413, U.S. Pat. No. 6,833,404, U.S. Pat. No. 5,021,499, U.S. Pat. No. 4,618,640 and U.S. Pat. No. 4,197,380 disclose tackifying resins for hot melt adhesive application.

U.S. Pat. No. 6,890,982, U.S. Pat. No. 6,060,550, U.S. Pat. No. 5,063,271 and U.S. Pat. No. 5,037,874 disclose waxes for hot melt adhesive application.

U.S. Pat. No. 4,576,985 and U.S. Pat. No. 4,197,380 disclose hot melt adhesives for low surface energy substrates.

SUMMARY

While known compositions and processes may be suitable for their intended purposes, and in fact materials of such known compositions can be used herein as appropriate, a need remains for improved adhesion promoters and adhesives containing adhesion promoters.

These and other improvements are accomplished by the adhesion promoters and adhesives described herein.

In embodiments, described is an adhesion promoter for hot melt adhesives and pressure sensitive adhesives, comprising a silane composition formed by admixing a hydrolytic silane compound with an aqueous buffer solution.

In embodiments, described is a hot melt adhesive or pressure sensitive adhesive including at least one adhesive promoter comprising a silane composition formed by admixing a hydrolytic silane compound with an aqueous buffer solution.

EMBODIMENTS

As explained above, it is known to apply release agents to the fuser roll to provide the necessary release of a substrate containing an image thereon from the fuser roll after the toner image has been formed on the substrate. Release agents are known to those of ordinary skill in the art, and include release agents such as disclosed in U.S. Publication No. 2006/0008727, U.S. Publication No. 2004/0185272 and U.S. Publication No. 2003/0108737, each of which is incorporated herein by reference in its entirety. As used herein, "substrate" refers to any media that may be printed on, such as paper, including synthetic paper, pre-print forms, plastic films, transparency, cardboard, cloth, etc.

Xerographic prints may be contaminated by a release agent such as silicone fuser oil due to the printing process. Some release agent may remain on a toner image that may cover any portion of the substrate and on the substrate itself. In other words, some release agent may remain on a final substrate having an image thereon and may at least partially cover a substrate having no toner image or a substrate having a toner image thereon. "Partially" refers to the release agent covering from above 0 percent to less than 100 percent of the substrate, such as from about 10 percent to about 90 percent or from about 20 percent to about 80 percent of the substrate. The release agent may chemically bond to the surface of the prints because of the reactive functional group such as amino or mercapto functional group in fuser oil during fusing process at high pressure and high temperature. The surface free energy (SFE) of the prints may thus dramatically drop from a range of higher than about 30 mN/m² for typical substrates such as paper to a range of from about 8 mN/m² to less than about 30 mN/m². Generally, commercially available hot melt adhesives bind to substrates having a SFE higher than about 30 mN/m².

Any release agent remaining on the substrate, with or without a toner image thereon, may be detrimental to an adhesive attempting to adhere to the substrate having a toner image. This is particularly important when the substrate is to be laminated or coated with a hot melt adhesive, such as an adhesive used in bookbinding. This release agent may also prevent materials utilizing adhesives, for example, POST-IT® notes, from adhering to the substrate.

Typical release agents used in releasing a substrate from a fuser roll in an imaging device include poly-ogranofunctional siloxanes, such as amino-functional silicone oils, such as methyl aminopropyl methyl siloxane, ethyl aminopropyl methyl siloxane, benzyl aminopropyl methyl siloxane, dodecyl aminopropyl methyl siloxane, aminopropyl methyl siloxane, and the like.

Disclosed herein is an adhesion promoter that promotes the adhesion of an adhesive to a substrate with surface free energy lower than 30 mN/m². The substrate may be at least partially covered by a release agent. The adhesion promoter may also promote adhesion of an adhesive to a substrate having no toner image or a substrate having a toner image without being covered by a release agent.

It is desirable to have an adhesive with a stable viscosity that is maintained constant during the application process. For example, the adhesive desirably has a stable viscosity at the application temperature, such as a temperature from about 100° C. to 200° C., such as from about 140° C. to about 190° C. or from about 150° C. to about 180° C.

An adhesive that incorporates a conventional adhesion promoter may encounter issues associated with the pot life of the adhesive. That is, the adhesive may not be able to be kept long enough in a hot pot to meet the requirements during the application process, for example in bookbinding applications. The viscosity of the adhesive containing a conventional adhesion promoter may continuously increase and cause operating problems.

It is thus desirable to have an adhesion promoter that can be added to a hot melt adhesive or pressure sensitive adhesive and at the same time maintain the thermal stability of the adhesive, or maintain a long enough pot life and constant viscosity of the adhesive during the application process.

A thermally stable adhesive is one that substantially maintains its viscosity and adhesion properties over a period of time. A stable viscosity, for example, is an increase or decrease in viscosity within 1000 cp over the aging process at the application temperature, such as from about 100 to about 800 cp over 8 hours at an application temperature or from about 200 to about 600 cp over 8 hours at an application temperature.

In embodiments, described is an adhesion promoter that includes a silane compound that is pretreated with an aqueous buffer solution before introduction into an adhesive.

In embodiments, the adhesion promoter before treatment may be a silane compound, for example, a silane compound such as an alkyloxysilane compound or a glycidoxy silane compound. Further examples include organic silane compounds, which may comprise at least one silane group represented by the following formula:

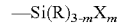

wherein R may be a $C_1$-$C_{30}$ hydrocarbyl including an alkyl, an aryl, a vinyl and the like, wherein the hydrocarbyl may further contain a halogen, nitrogen, oxygen or sulfur atom. Illustrative examples of R may include methyl, ethyl, propyl, octyl, phenyl, methacryloxypropyl, aminopropyl, aminoethylaminopropyl, phenylaminopropyl, chloropropyl, mercaptopropyl, acryloxypropyl, 3-glycidoxypropyl, trifluoropropyl, heptadecafluorodecyl, and isocyanatopropyl group and the like. X may represent a hydrolyzable functional group, a $C_1$-$C_{20}$ alkoxy group, a hydroxy group, a carboxylate group, an alkoxy group, an arylalkyloxy group, and an aryloxy group, a halogen or a hydrogen atom, and m is an integer of 1, 2 or 3.

In embodiments, R may be a non-hydrolyzable organic group, X may be a hydrolytic group and m may be an integer of 1, 2 or 3. X may include a halide, a hydroxyl group, a carboxylate group, an alkoxy group, an arylalkyloxy group and an aryloxy group. The hydrolytic silane compound may contain in total two of the hydrolytic X group.

In embodiments, the hydrolytic silane compound may include a functional group. Examples of functional groups may include, for example, an amino group, a mercapto group, an epoxy group and a vinyl group.

Examples of silane compounds suitable for use herein include aminoalkylsilane, mercaptoalkylsilane and mixtures thereof, for example, 4-aminobutyltriethoxysilane, 1-amino-2-(dimethylethoxysilyl)propane, N-(2-aminoethyl)-3-aminoisobutyldimethylmethoxysilane, N-(2-aminoethyl)-3-aminoisobutyldimethylmethoxysilane, (aminoethylaminomethyl)phenethyltrimethoxysilane, N-(2-aminoethyl)-3-aminopropylmethyldimethoxysilane, N-(2-aminoethyl)-3-aminopropylsilanetriol, N-(2-aminoethyl)-3-aminopropyltriethoxysilane, N-(2-aminoethyl)-3-aminopropyltrimethoxysilane, N-aminoethyl-AZA-2,2,4-trimethylsilacyclopentane, N-(6-aminohexyl)aminomethyl-trimethoxysilane, N-(6-aminohexyl)aminopropyltrimethoxysilane, N-(2-aminoethyl)-11-aminoundecyl-trimethoxysilane, 3-aminopropylmethylbis(trimethylsiloxy)silane, 3-aminopropyldimethylethoxysilane, 3-aminopropyltrimethoxysilane, 3-aminopropyltris(methoxyethoxyethoxy)silane, 3-(triethoxysilyl)propylsuccinic anhydride, tris(3-trimethoxysilylpropyl)iso-cyanurate, (3-trimethoxysilylpropyl)diethylene-triamine, methyltrichlorosilane, dimethyldichlorosilane, methyltriethoxysilane, ethyltrichlorosilane, ethyltrimethoxysilane, dimethyldimethoxysilane, methyltriethoxysilane, ethyltriethoxysilane, propyltrimethoxysilane, amino silane hydrochloride, 3-glycidoxypropyl trimethoxysilane (Z-6040, available from Dow Corning; KBM 403, available from Shin-Etsu), methyltrimethoxysilane (Z-6070, available from Dow Corning: KBM 13, available from Shin-Etsu), methacryloxypropyltrimethoxysilane (Z-6030, available from Dow Corning; KBM502, available from Shin-Etsu), aminopropyltrimethoxysilane (Z-6011, available from Dow Corning; KBM903, available from Shin-Etsu), aminoethylaminopropyltrimethoxysilane (KBM603, available from Shin-Etsu or DOW Z 6032, available from Dow Corning; KBM603, available from Shin-Etsu), trifluoropropyltrimethoxysilane (KBM7103, available from Shin-Etsu), heptadecafluorodecyltrimethoxysilane (KBM7803, available from Shin-Etsu), isocyanatopropyltriethoxysilane (KBE9007, available from Shin-Etsu), aminopropyltriethoxysilane (KBE903, available from Shin-Etsu), aminoethylaminopropyltriethoxysilane (KBE603, available from Shin-Etsu), alkyltrimethoxysilane (DOW HV 10, available from Dow Korning), and a coating having trifluoropropy trim-ethoxysilane, vinylmethoxysilane, tetra(2-methoxyethoxy)silane (DOW 4040 Prime Coat, available from Dow Corning), mixtures thereof and the like.

The adhesion promoter disclosed herein may include more than one silane compound, for example, the adhesion promoter may include from about 1 to about 5 silane compounds, such as from about 1 to about 3 silanes.

In embodiments, the silane compound is admixed with aqueous buffer solution before incorporation into an adhesive. The aqueous buffer solution may include a buffer agent. The aqueous buffer solution is made by dissolving the buffer agent into distilled water. The buffer agent may be an inorganic salt, for example an alkali metal phosphate, an alkali metal sulfite and the like or an aqueous solution of an inorganic salt. Other suitable buffer agents include aqueous solutions of potassium phosphate monobasic, potassium phosphate dibasic, sodium hydrogen sulfite, mixtures thereof and the like, for example dissolved in distilled water.

In embodiments, the aqueous buffer solution may be prepared to form from about 1% to about 50% by weight buffer solution, such as, from about 5% to about 25% by weight buffer solution, and for example from about 5% to about 15% by weight buffer solution.

In embodiments, the pH of the buffer solution may be, for example, from about 2 to about 10, such as from about 4 to about 9.

In embodiments, the aqueous buffer solution may be added to the silane compound, for example in a silane to buffer solution ratio from 1:0.005 to 1:0.5, such as a ratio of 1:0.15 and for example a ratio of 1:0.35. The buffer solution may be added to the silane compound while agitating the silane compound at room temperature. The silane compound temperature goes up after the adding of the buffer solution because this may be an exothermic reaction process. The adhesion promoter may be kept agitating from about 1 hour to about 3 hours before it is incorporated into hot melt adhesives or pressure sensitive adhesives. The shelf life for the admixed silane may be as long as three days or longer at room temperature.

The admixed silane adhesion promoter described herein provides at least two beneficial functions in order to promote adhesion of the adhesive to the substrate: (1) a reactive silicone group, that is, a group reactive with silicone, for bonding with the Xerographic print or substrate, such as a methoxy or an ethoxy group, and (2) an organic component for compatibility with the adhesive.

The admixed adhesion promoter may be utilized in a variety of ways to promote the adhesion of an adhesive to a substrate. The admixed adhesion promoter promotes adhesion to the substrate in locations where there is a toner image, where there is not toner image, and where there is a toner image at least partially covered by a release agent. In other words, the adhesion promoter promotes adhesion of an adhesive to a substrate, regardless if the substrate has a toner image thereon, has release agent thereon, or if the substrate has a toner image thereon, that is at least partially covered by a release agent.

In embodiments, the admixed adhesion promoter may be used as a separate coating on the substrate to be used as a primer, dispersed within a release agent, or incorporated into an adhesive.

In embodiments, the admixed adhesion promoter may be added directly to the adhesive of the laminate or the bookbinding material, such as into pressure sensitive adhesive formulations or hot melt adhesive formulations. The adhesive comprises a hot melt adhesive or pressure sensitive adhesive and an adhesion promoter pretreated with an aqueous buffer solution.

Suitable hot melt adhesives for use herein include most commercially available hot melt adhesive, such as polyethylene, poly(ethylene/vinyl acetate), polystyrene, polyamide, a polyolefin based polymer, polyester, phenol-formaldehyde resin, etc., of a homopolymer or a block copolymer based hot melt adhesives. Other examples of commercially available hot melt adhesives include for example HM220 available from Horizon and US661 manufactured by U.S. Adhesives.

When the admixed silane compound used as an adhesion promoter is added to a commercially available hot melt adhesive, the first step is to heat the adhesive to the application temperature until the adhesive is substantially melted or flows. Then the adhesion promoter is slowly added to the adhesive while keeping the application temperature and the speed of the agitation controlled. The application temperature is determined by the adhesive formulation. The speed of the agitation may be controlled from about 100 to about 500 rpm.

The adhesion promoter may be added to the adhesive formulation in amounts of from about 0.05 weight percent to about 5 weight percent of the adhesive formulation, such as from about 0.5 weight percent to about 3 weight percent or from about 1 weight percent to about 2 weight percent of the adhesive formulation.

By chemically bonding to both the adhesive and the substrate, the pretreated adhesion promoter promotes the adhesion of an adhesive to a substrate having an oil contaminated surface with a Surface Free Energy (SFE) from less than about 30 mN/m$^2$, such as from about 8 mN/m$^2$ to less than about 30 mN/m$^2$, such as from about 10 mN/m$^2$ to about 28 mN/n2 or from about 15 mN/m$^2$ to about 25 mN/m$^2$.

In embodiments, the adhesive may display a viscosity ranging for example from about 1,000 centipose to about 20,000 centipose at temperatures ranging for example from about 120° C. to about 200° C.

Suitable hot melt adhesives formulation for use herein may include thermoplastics or materials which appear to be thermoplastic including components such as polymer resins, tackifiers, waxes, plasticizers, antioxidants and filler or combinations thereof.

In embodiments, an optional plasticizer may be added to the commercially available hot melt adhesives or pressure sensitive adhesives. The plasticizer may be added before or after the addition of an adhesion promoter to the adhesive, but it is more desirable to add the plasticizer before the addition of the adhesion promoter to lower the initial viscosity of the adhesive.

Examples of the optional plasticizer suitable for use herein may include, for example, paraffinic linear oil, naphthenic cycloaliphatic oil, aromatic ring containing oil, white mineral oil commercially available as KAYDOL oil, polyisobutylene commercially available as INDOPOL H300, pentaerythritol tetrabenzoate commercially available as BENZOFLEX S552

(Velsicol Chemical Corporation), trimethyl titrate, commercially available as CITROFLEX 1 (Monflex Chemical Company), N,N-dimethyl oleamide, commercially available as HALCOMID M-18-OL (C. P. Hall Company), a benzyl phthalate, commercially available as SANTICIZER 278 (Ferro Corporation), mixtures thereof and the like.

In embodiments, the optional plasticizer may be added to the adhesive, for example, in the amount of from about 1 to about 20% by weight, such as from about 5 to about 15% by weight.

The most common general purpose hot melt adhesive is based on ethylene vinyl acetate (EVA) resins. Other polymers commonly used in hot melt adhesives and pressure sensitive adhesives include low density polyethylene, poly(ethylene/vinyl acetate), polyvinyl alcohol, polystyrene, polyamides, polyalkylene oxide, polyacrylate, ethylene acrylic copolymers, polypropylene (atactic), phenoxy resins, polyesters, APAO, polyesteramides, polyparaffins, polyurethanes, polyurethane prepolymers, thermalplastic acrylic polymers butyl rubbers, polyvinyl acetate and copolymers, styrenic block copolymers (SIS, SBS, SEBS), phenol-formaldehyde resin of polymer or block copolymer, natural rubber, and a copolymer thereof etc.

Examples of suitable polymer resins that may be optionally used in the hot melt adhesives or pressure sensitive adhesives formulation or added to the commercially available adhesives include poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethyl acrylate-butadiene), poly(propyl acrylate-butadiene), poly(butyl acrylate-butadiene), poly(methyl methacrylate-isoprene), poly(ethyl methacrylate-isoprene), poly(propyl methacrylate-isoprene), poly(butyl methacrylate-isoprene), poly(methyl acrylate-isoprene), poly(ethyl acrylate-isoprene), poly(propyl acrylate-isoprene) and poly(butyl acrylate-isoprene), poly(styrene-butadiene), poly(methylstyrene-butadiene), poly(styrene-isoprene), poly(methylstyrene-isoprene), poly(styrene-propyl acrylate), polystyrene-butyl acrylate), poly(styrene-butadiene-acrylic acid), poly(styrene-butadiene-methacrylic acid), poly(styrene-butadiene-acrylonitrile-acrylic acid), polystyrene-butyl acrylate-acrylic acid), poly(styrene-butyl acrylate-methacrylic acid), poly(styrene-butyl acrylate-acrylononitrile), and poly(styrene-butyl acrylate-acrylononitrile-acrylic acid), block copolymer such as styrene-isoprene-styrene (SIS) or styrene-butadiene-styrene (SBS), polyester or mixtures thereof and the like.

In embodiments, the polymer resin content in the hot melt adhesives or pressure sensitive adhesives may be in the amount of from about 20 to about 50% by weight, such as from about 25 to about 35% by weight.

Examples of optional tackifiers used in hot melt adhesives and pressure sensitive adhesives include aliphatic and aromatic resins, hydrocarbons and hydrogenated hydrocarbons or mixed C5/C9 resins, modified rosin, natural tackifiers are rosin acid derivatives and their esters, terpene resins, pure monomers, hydrogenated pure monomers etc. and combinations thereof. Examples of the optional tackifier suitable for use herein may be Eastotac H100-W, Regalite S1100, Foralyn 110 from Eastman Chemical.

In embodiments, the optional tackifier may be added to the adhesive, for example, in the amount of from about 5 to about 30% by weight.

Examples of the optional wax suitable for use herein may include natural and synthetic waxes. Examples of natural waxes may include animal wax such as beeswax and lanolin wax, vegetable wax such as carnauba wax, mineral wax such as montan wax and paraffin wax, microcrystalline wax and slack wax. Examples of synthetic waxes suitable for used herein may include polyethylene wax such as homopolymer wax and copolymer wax and modified polymer wax, polypropylene wax such as homopolymer wax and modified polymer wax, semicrystalline flexible polyolefines, and Fisher-Tropsch wax such as homopolymer wax and modified polymer wax.

In embodiments, the optional wax may be added to the adhesive, for example, in the amount of from about 5 to about 20% by weight. In embodiments, the wax may have a melting point for example from about 50° C. to about 150° C.

Examples of the optional antioxidant suitable for use herein include primary and secondary antioxidant or multifunctional antioxidant, hydroxylamines, N,N'-hexamethylene bis(3,5-di-tert-butyl-4-hydroxy hydrocinnamamide) (IRGANOX 1098, available from Ciba-Geigy Corporation), 2,2-bis(4-(2-(3,5-di-tert-butyl-4-hydroxyhydrocinnamoyloxy)) ethoxyphenyl)propane (TOPANOL-205, available from ICI America Corporation), tris(4-tert-butyl-3-hydroxy-2,6-dimethyl benzyl)isocyanurate (CYANOX 1790, 41,322-4, LTDP, Aldrich D12,840-6), 7,2'-ethylidene bis(4,6-di-tert-butylphenyl)fluoro phosphonite (ETHANOX-398, available from Ethyl Corporation), tetrakis(2,4-di-tert-butylphenyl)-4,4'-biphenyl diphosphonite (ALDRICH 46,852-5; hardness value 90), pentaerythritol tetrastearate (TCI America #PO739), tributylammonium hypophosphite (Aldrich 42,009-3), 2,6-di-tert-butyl-4-methoxyphenol (Aldrich 25,106-2), 2,4-di-tert-butyl-6-(4-methoxybenzyl)phenol (Aldrich 23,008-1), 4-bromo-2,6-dimethylphenol (Aldrich 34,951-8), 4-bromo-3,5-didimethylphenol (Aldrich B6,420-2), 4-bromo-2-nitrophenol (Aldrich 30,987-7), 4-(diethyl aminomethyl)-2,5-dimethylphenol (Aldrich 14,668-4), 3-dimethylaminophenol (Aldrich D14,400-2), 2-amino-4-tert-amylphenol (Aldrich 41,258-9), 2,6-bis(hydroxymethyl)-p-cresol (Aldrich 22,752-8), 2,2'-methylenediphenol (Aldrich B4,680-8), 5-(diethylamino)-2-nitrosophenol (Aldrich 26,951-4), 2,6-dichloro-4-fluorophenol (Aldrich 28,435-1), 2,6-dibromo fluoro phenol (Aldrich 26,003-7), α-trifluoro-o-cresol (Aldrich 21,979-7), 2-bromo-4-fluorophenol (Aldrich 30,246-5), 4-fluorophenol (Aldrich F1,320-7), 4-chlorophenyl-2-chloro-1,1,2-tri-fluoroethyl sulfone (Aldrich 13,823-1), 3,4-difluoro phenylacetic acid (Aldrich 29,043-2), 3-fluorophenylacetic acid (Aldrich 24,804-5), 3,5-difluoro phenylacetic acid (Aldrich 29,044-0), 2-fluorophenylacetic acid (Aldrich 20,894-9), 2,5-bis (trifluoromethyl)benzoic acid (Aldrich 32,527-9), ethyl-2-(4-(4-(trifluoromethyl)phenoxy)phenoxy)propionate (Aldrich 25,074-0), tetrakis (2,4-di-tert-butyl phenyl)-4,4'-biphenyl diphosphonite (Aldrich 46,852-5), 4-tert-amyl phenol (Aldrich 15,384-2), 3-(2H-benzotriazol-2-yl)-4-hydroxy phenethylalcohol (Aldrich 43,071-4), NAUGARD 76, NAUGARD 445, NAUGARD 512, AND NAUGARD 524 (manufactured by Uniroyal Chemical Company), and the like, as well as mixtures thereof.

In embodiments, the optional antioxidant may be added to the adhesive, for example, in the amount of from about 0.1% to about 2%.

Examples of the optional filler suitable for use herein include titanium dioxide, calcium carbonates, zinc oxide, clays, talcs and barium sulfate.

In embodiments, the optional filler may be added to the adhesive, for example, in the amount of from about 0.1% to about 5%.

In embodiments, the hot melt adhesive or pressure sensitive adhesive may be applied to a substrate, and the adhesion promoter may be present at the interface between the substrate and the adhesive. The adhesive may be used to bind such articles.

In embodiments, the substrate may be a Xerographic print, including Xerographic prints contaminated with fuser oil, such as silicone oil. The substrate may include cast coat paper, gloss or silk coated paper, matte or plain paper, synthetic paper and offset pre-print forms. Other suitable articles that may be bound include, for example, books and laminating cards.

Embodiments described above will now be further illustrated by way of the following examples.

EXAMPLES

Examples 1-3

Preparation of Buffer Solutions

Buffer Solution 1: Potassium phosphate dibasic ($K_2HPO_4$) powder (10 grams) was dissolved in 90 g of distilled water at room temperature.

Buffer Solution 2: Sodium hydrogen sulfite ($NaHSO_3$) powder (10 grams) was dissolved in 90 g of distilled water at room temperature.

Buffer Solution 3: Potassium phosphate monobasic ($KH_2PO_4$) powder (10 grains) was dissolved in 90 g of distilled water at room temperature.

Examples 4-6

Preparation of Silane Compositions

Silane Promoter 1: Into 50 grams of Silane A-2120 [N-(2-aminoethyl)-3-aminopropylmethyldimethoxysilane from GE silicones] was added slowly 8 grams of Buffer Solution 1 with proper agitation at room temperature. The resulting silane composition was kept stirring for 3 hours before use.

Silane Promoter 2: Into 50 grams of Silane A-2120 [N-(2-aminoethyl)-3-aminopropylmethyldimethoxysilane from GE silicones] was added slowly 8 grams of Buffer Solution 2 with proper agitation at room temperature. The resulting silane composition was kept stirring for 3 hours before use.

Silane Promoter 3: Into 50 grams of Silane A-2120 [N-(2-aminoethyl)-3-aminopropylmethyldimethoxysilane from GE silicones] was added slowly 8 grams of Buffer Solution 3 with proper agitation at room temperature. The resulting silane composition was kept stirring for 3 hours before use.

Examples 7-9

Preparation of Hot Melt Adhesives

Adhesive 1: 100 g of HM220 (a hot melt adhesive available from HORIZON) was heated to 180° C. in a paint can with a heating mantle. Into the melt adhesive, 5 grams of plasticizer KAYDOL white mineral oil (from Crompton Corp.) was added with an agitation speed of 250 rpm, followed by slow addition of 2.5 grams of the Silane Promoter 1 over about 10 minutes. The resulting adhesive was stirred at 180° C. for another 30 minutes before it was discharged.

Adhesive 2: 100 g of HM220 (a hot melt adhesive available from HORIZON) was heated to 180° C. in a paint can with a heating mantle. Into the melt adhesive, 5 grams of plasticizer KAYDOL white mineral oil (from Crompton Corp.) was added with an agitation speed of 250 rpm, followed by slow addition of 2.5 grams of the Silane Promoter 2 over about 10 minutes. The resulting adhesive was stirred at 180° C. for another 30 minutes before it was discharged.

Adhesive 3: 100 g of HM220 (a hot melt adhesive available from HORIZON) was heated to 180° C. in a paint can with a heating mantle. Into the melt adhesive, 5 grams of plasticizer KAYDOL white mineral oil (from Crompton Corp.) was added with an agitation speed of 250 rpm, followed by slow addition of 2.5 grams of the Silane Promoter 3 over about 10 minutes. The resulting adhesive was stirred at 180° C. for another 30 minutes before it was discharged.

Comparison Example 1

A control hot melt adhesive was prepared as follow: 100 g of HM220 (a hot melt adhesive available from HORIZON) was heated to 180° C. in a paint can with a heating mantle. Into the melt adhesive, 2.5 grams of Silane A-2120 was added over about 10 minutes with an agitation speed of 250 rpm. The resulting adhesive was stirred at 180° C. for another 30 minutes before it was discharged.

Testing of Adhesive

Viscosity: The viscosity of the hot melt adhesives was measured by AR2000 Rheometer in a temperature range of 180° C. to 120° C. at a shear rate of 100 (1/s).

Thermal Stability: The adhesive thermal stability was evaluated as follows: an adhesive sample was kept in oven at 180° C., and its viscosity was monitored over 1~8 hours.

The properties of the adhesives are summarized in Table 1.

TABLE 1

The Thermal Stability of Adhesives with adhesion promoter

| Aging Time (hrs) | Viscosity (cp)@180° C. | | | |
|---|---|---|---|---|
| (180° C. in Oven) | Control | Adhesive 1 | Adhesive 2 | Adhesive 3 |
| 0 | 4525 | 5222 | 5123 | 5238 |
| 2 | 6794 | 4943 | 5170 | 4988 |
| 8 | 8105 | 5223 | 5632 | 5396 |
| Δη from 0 to 8 hrs | 3580 | 1 | 509 | 158 |

Δη equals the change in viscosity over the indicated aging time.

By adding pure silane A-2120 without admixed with buffer solution, the viscosity increased more than 3500 cp after the adhesive was kept in an oven at an application temperature of 180° C. for 8 hours.

After Silane A-2120 was admixed with buffer solutions, the viscosity variation can be controlled within 500 cp after the adhesive was kept in an oven at an application temperature of 180° C. for 8 hours. The thermal stability of the adhesives is improved by admixing the silane with a buffer solution.

Gluability

Test Procedure: The gluability was tested by using a home-made tester that simulates a commercial hot melt adhesive binding application. The fuser oil contaminated sheets used for the gluability test were generated by passing a paper (letter size 8.5"×11") through a fusing fixture using typical silicone fuser oil. The paper typically contains from about 10 to about 60 micrograms of fuser oil. Onto the oil contaminated paper was applied a hot melt adhesive, and laminated with a second piece of paper to form a bound article. Paper tear (the measurement of gluability) is measured by manually separating the article, and visually inspecting the area of the fiber tear: 0% means that there is no paper fiber tear, indicating poor binding adhesion, and 1(31% means good and complete adhesion.

Test Results

Comparison Example 2

Gluability Test Results on Xerographic Prints Printed on Coated and Uncoated Papers

TABLE 2

Gluability comparison between commercially available hot melt adhesives and admixed silane promoted hot melt adhesive 3.

| Xerographic Prints Contaminated by Xerox Fuser Fluid 8R13030 | Paper Fiber Tear (%) | | |
|---|---|---|---|
| | HM220 Commercial Glue | US661 Commercial Glue | Adhesive 3 |
| 10 pt KromeKote-F/F | 20 | 40 | 100 |
| 10 pt KromeKote-B/B | 17.5 | 47.5 | 100 |
| 10 pt CornWall-F/F | 0 | 0 | 100 |
| 10 pt CornWall-B/B | 50 | 85 | 99 |
| Color Xpressions+ | 5 | 17.5 | 97.5 |
| 10pt Elite Digital Color Gloss Cover | 25 | 50 | 95 |
| 110 lb Luna Matte | 0 | 20 | 95 |
| 80 lb Digital Color Elite Gloss Text | 0 | 5 | 82.5 |
| 80 lb Digital Color Elite Silk Text | 0 | 5 | 80 |
| 110 lb Digital Color Elite Gloss Cover | 0 | 27.5 | 100 |

Comparison Example 3

Gluability Test Results on Xerographic Prints Printed on Offset Pre-Prints Forms

TABLE 3

Gluability comparison between commercially available hot melt adhesive and admixed silane promoted hot melt adhesives 1-3.

| Xerographic Prints Contaminated by Xerox Fuser Fluid 8R12936 | Paper Fiber Tear (%) | | | |
|---|---|---|---|---|
| | HM220 Commercial Glue | Adhesive 1 | Adhesive 2 | Adhesive 3 |
| RSG Offset Pre-Print Form | 0 | 77.5 | 55 | 72.5 |

TABLE 4

Gluability comparison between commercially available hot melt adhesive and admixed silane promoted hot melt adhesive 3.

| Xerographic Prints Contaminated by Xerox Fuser Fluid 8R12936 | Paper Fiber Tear (%) | |
|---|---|---|
| | HM220 Commercial Glue | Adhesive 3 |
| Vanguard_Green | 0 | 100 |
| Foundation_Light Green | 0 | 85 |
| Seagate_Light Gray | 0 | 100 |
| Vanguard_Dark Grey | 0 | 95 |
| QVC_Green | 0 | 92.5 |

By adding a small amount of the admixed silicone compound A-2120 to a commercially available adhesive such as HM220, the fiber tear increases from 0 to about 100% on Xerographic prints printed on offset presses pre-print forms. The gluability test results showed that the adhesives with admixed silane compound as an adhesion promoter can bind Xerographic prints, which are generated using high content functional group fuser oil.

Example 10

Surface Free Energy Measurements on Substrates

The surface free energy SFE of the Xerographic prints generated on fusing fixture was lowered dramatically by contaminated substrates or media or by increasing the content of functional group in fuser oil.

Procedures on Contact Angle Measurement

Contact angles are measured by Fibro DAT1100 at temperature 23° C. and RH 50%. Before the measurement, the substrates or media was conditioned in room with 23° C. and RH 50% for more than 8 hrs. Three solvents are used for the CA measurement, Water, Formamide, Diiodomethane.

Surface Free Energy Test Results

Surface Free Energy is calculated by LW (Lewis) Acid/Base Method.

TABLE 5

Surface Free Energy comparison on No Oil, Xerox Fuser Fluid 8R12936, Xerox Fuser Fluid 8R13030 fuser oil Contaminated Offset preprint forms

| Paper Description | No Oil | Xerox Fuser Fluid 8R12936 | Xerox Fuser Fluid 8R13030 |
|---|---|---|---|
| Vanguard (RSG)_Green | 42.82 | 15.33 | 12.55 |
| Vanguard-Dark Green | 44.33 | 14.24 | 11.93 |
| Gateway-Light Green | 31.46 | 28.55 | 15.61 |
| Seagate-Light Green | 40.47 | 12.49 | 10.99 |
| Fundation-Light Green | 43 | 18.54 | 11.62 |
| QVC-Green Side | 42.61 | 13.28 | 11.37 |

TABLE 6

Surface Free Energy comparison on Xerox Fuser Fluid 8R12936, Xerox Fuser Fluid 8R13030 fuser oil contaminated cast coat papers, gloss and silk coated papers

| Paper Description | Xerox Fuser Fluid 8R12936 | Xerox Fuser Fluid 8R13030 |
|---|---|---|
| 10 pt KK_Coated Side | 30.71 | 21.84 |
| 10 pt KK_Uncoated Side | 24.51 | 20.66 |
| 10 pt CW_Coated Side | 27.20 | 23.06 |
| 10 pt CW_Uncoated Side | 40.47 | 8.92 |
| 10 pt Elite Digital Color Gloss | 26.14 | 18.33 |
| Color Xpressions+ | 17.71 | 12.99 |
| 110 lb Luna Matte | 45.43 | 25.64 |

It will be appreciated that various of the above-disclosed and other features and functions, or alternatives thereof, may be desirably combined into many other different systems or applications. Also, various presently unforeseen or unanticipated alternatives, modifications or improvements therein may be subsequently made by those skilled in the art, and are also intended to be encompassed by the following claims. Unless specifically recited in the claim, steps or components of claims should not be implied or imported form the specification or any other claims as to any particular order, number, position, size, shape, angel, color, or material.

What is claimed is:

1. An adhesion promoter for hot melt adhesives and pressure sensitive adhesives, comprising a silane composition formed by admixing a hydrolytic silane compound with an aqueous buffer solution, wherein the aqueous buffer solution comprises buffer agent and water, and wherein a ratio of the hydrolytic silane to the water in the aqueous buffer solution ranges from about 1:0.05 to about 1:0.5 by weight.

2. The adhesion promoter according to claim 1, wherein the hydrolytic silane compound comprises at least one silane group of $-Si(R)_{3-m}X_m$, wherein R is a non-hydrolyzable organic group, X is a hydrolytic group and m is an integer of 1 to 3.

3. The adhesion promoter according to claim 2, wherein X is selected from the group consisting of a halide, a hydroxyl group, a carboxylate group, an alkoxy group, an arylalkyloxy group, and an aryloxy group.

4. The adhesion promoter according to claim 2, wherein the hydrolytic silane compound contains in total two of the hydrolytic X group.

5. The adhesion promoter according to claim 1, wherein the hydrolytic silane compound further comprises a functional group selected from the group consisting of an amino group, a mercapto group, an epoxy group and a vinyl group.

6. The adhesion promoter according to claim 1, wherein the hydrolytic silane compound is selected from the group consisting of an aminoalkylsilane, a mercaptoalkylsilane or mixtures thereof.

7. The adhesion promoter according to claim 1, wherein the hydrolytic silane compound is selected from the group consisting of N-(2-aminoethyl)-3-aminopropylmethyldimethoxysilane, N-(2-aminoethyl)-3-aminopropyltrimethoxysilane, N-(2-aminoethyl)-3-aminopropylethyldiethoxysilane, N-(2-aminoethyl)-3-aminopropyltriethoxysilane 4-Aminobutyltriethoxysilane, 1-Amino-2-(Dimethylethoxysilyl)propane, N-(2-aminoethyl)-3-aminoisobutyldimethylmethoxysilane, N-(2-aminoethyl)-3-aminoisobutyldimethylmethoxysilane, (aminoethylaminomethyl)phenethyltrimethoxysilane, N-(2-aminoethyl)-3-aminopropylsilanetriol, N-(6-aminohexyl)aminomethyl-trimethoxysilane, N-(6-aminohexyl)aminopropyl-trimethoxysilane, N-(2-aminoethyl)-11-aminoundecyl-trimethoxysilane, 3-aminopropylmethylbis(trimethylsiloxy)silane, 3-aminopropyldimethylethoxysilane, 3-aminopropyltrimethoxysilane, 3-aminopropyltris(methoxyethoxyethoxy)silane, (3-trimethoxysilylpropyl)diethyleno-triamine, 3-aminopropyltrimethoxysilane, 3-aminopropyltriethoxysilane, aminoethylaminopropyltrimethoxysilane, aminoethylaminopropyltriethoxysilane, or mixtures thereof.

8. The adhesion promoter according to claim 1, wherein the buffer agent comprises an inorganic salt or an aqueous solution of an inorganic salt.

9. The adhesion promoter according to claim 1, wherein the buffer agent is an alkali metal phosphate or an alkali metal sulfite.

10. The adhesion promoter according to claim 1, wherein the buffer agent is selected from the group consisting of potassium phosphate dibasic, potassium phosphate monobasic, sodium hydrogen sulfite, and mixtures thereof.

11. The adhesion promoter according to claim 1, wherein the aqueous buffer solution has a pH value ranging from about 2 to about 10.

12. The adhesion promoter according to claim 1, wherein the ratio of the hydrolytic silane to the buffer agent in buffer solution ranges from about 1:0.005 to about 1:0.25 by weight.

13. A process of preparing a hot melt adhesive comprising at least substantially melting the hot melt adhesive and adding the adhesion promoter of claim 1 to the hot melt adhesive.

14. The process of claim 13, wherein the hot melt adhesive is a polyethylene, poly(ethylene/vinyl acetate), polystyrene, polyamide, phenol-formaldehyde resin of polymer or block copolymer based hot melt adhesive.

15. The process of claim 13, further comprising adding an optional plasticizer to the hot melt adhesive.

16. The process of claim 13, further comprising adding a polymer resin to the hot melt adhesive.

17. The process of claim 16, wherein the polymer resin is selected from the group consisting of a polyparaffin, a polyacrylate, a polyester, a polyurethane, a polystyrene, a polyamide, a polyvinyl acetate, a polyvinyl alcohol, a polyalkylene oxide, natural rubber, and a copolymer comprised thereof.

18. The process of claim 13, further comprising adding a tackifier to the hot melt adhesive.

19. The process of claim 18, wherein the tackifier is selected from the group consisting of natural rosin, modified rosin, hydrocarbons and hydrogenated hydrocarbons, pure monomers and hydrogenated pure monomers.

20. A process of forming an adhesion promoter comprising pretreating a silane compound prior to the forming of the adhesion promoter with aqueous buffer solution, wherein the aqueous buffer solution comprises water and buffer agent, wherein the aqueous buffer solution is 5% to 20% by weight buffer agent, and wherein a ratio of silane to the water in the aqueous buffer solution is from about 1:0.05 to about 1:0.5 by weight.

21. The process according to claim 20, wherein the pretreating comprises adding at least one aqueous buffer solution to the silane compound while agitating the silane compound.

22. The process according to claim 20, wherein the silane compound is selected from the group consisting of an aminoalkylsilane compound, a mercaptoalkylsilane, and mixtures thereof.

23. The process according to claim 20, wherein the buffer agent comprises an inorganic salt or an aqueous solution of an inorganic salt.

24. The process according to claim 23, wherein the inorganic salt is selected from the group consisting of an alkali metal phosphate and an alkali metal sulfite.

25. The process according to claim 20, further comprising adding the pretreated silane compound to a melted hot melt adhesive or a pressure sensitive adhesive.

* * * * *